(12) United States Patent
Kubo

(10) Patent No.: US 7,927,892 B2
(45) Date of Patent: Apr. 19, 2011

(54) THERMAL TREATMENT APPARATUS, THERMAL TREATMENT METHOD AND METHOD OF MANUFACTURING SEMICONDUCTOR DEVICE

(75) Inventor: Tomohiro Kubo, Kawasaki (JP)

(73) Assignee: Fujitsu Semiconductor Limited, Yokohama (JP)

(*) Notice: Subject to any disclaimer, the term of this patent is extended or adjusted under 35 U.S.C. 154(b) by 284 days.

(21) Appl. No.: 12/246,055

(22) Filed: Oct. 6, 2008

(65) Prior Publication Data

US 2009/0093071 A1    Apr. 9, 2009

(30) Foreign Application Priority Data

Oct. 9, 2007  (JP) ................................ 2007-263720

(51) Int. Cl.
*H01L 21/00* (2006.01)

(52) U.S. Cl. .............. 438/7; 438/5; 438/6; 438/8; 438/9; 438/10; 438/11; 438/12; 438/13; 438/16; 438/808; 257/E21.53; 392/407; 362/310; 362/217; 362/241; 362/260; 362/514; 362/516; 362/518

(58) Field of Classification Search .................. 438/5–7, 438/8–13, 16, 808; 257/E21.53; 392/407; 362/310, 217, 241, 260, 514, 516, 518
See application file for complete search history.

(56) References Cited

U.S. PATENT DOCUMENTS

| | | | | |
|---|---|---|---|---|
| 4,601,576 A * | 7/1986 | Galbraith | .................... | 356/237.3 |
| 5,465,145 A * | 11/1995 | Nakashige et al. | ........ | 356/237.5 |
| 5,465,154 A * | 11/1995 | Levy | .............................. | 356/632 |
| 5,942,763 A * | 8/1999 | Mukogawa | ............... | 250/559.44 |
| 6,214,734 B1 * | 4/2001 | Bothra et al. | .................. | 438/692 |
| 6,228,277 B1 * | 5/2001 | Kornblit et al. | .................. | 216/60 |
| 6,520,668 B1 * | 2/2003 | Reiss | .............................. | 362/516 |
| 6,552,778 B1 * | 4/2003 | Konagaya | ........................ | 355/71 |
| 6,594,446 B2 * | 7/2003 | Camm et al. | .................. | 392/416 |
| 6,654,111 B2 * | 11/2003 | Isozaki et al. | ............... | 356/237.3 |
| 6,750,976 B2 * | 6/2004 | Eriguchi | ........................ | 356/630 |
| 6,771,364 B2 * | 8/2004 | Isozaki et al. | ............... | 356/237.2 |
| 7,230,709 B2 | 6/2007 | Kusuda | | |
| 7,236,847 B2 * | 6/2007 | Marella | ......................... | 700/110 |
| 7,255,899 B2 * | 8/2007 | Kusuda | ......................... | 427/559 |
| 7,319,518 B2 * | 1/2008 | Leonard et al. | ............. | 356/237.2 |
| 7,327,947 B2 * | 2/2008 | Kusuda | ......................... | 392/416 |
| 7,534,977 B2 * | 5/2009 | Yamazaki | ..................... | 219/390 |
| 7,700,382 B2 * | 4/2010 | Jin et al. | .......................... | 438/16 |
| 2002/0021438 A1 * | 2/2002 | Isozaki et al. | ............... | 356/237.5 |
| 2002/0141182 A1 * | 10/2002 | Holten | .......................... | 362/217 |
| 2004/0077185 A1 * | 4/2004 | Dairiki | .......................... | 438/795 |
| 2007/0003259 A1 | 1/2007 | Kaihori | | |
| 2008/0273337 A1 * | 11/2008 | Hirose | ........................... | 362/310 |

FOREIGN PATENT DOCUMENTS

| | | |
|---|---|---|
| JP | 2005-39213 A | 2/2005 |
| JP | 2005-207997 A | 8/2005 |
| JP | 2007-13047 A | 1/2007 |

* cited by examiner

*Primary Examiner* — Fernando L Toledo
*Assistant Examiner* — Ankush k Singal
(74) *Attorney, Agent, or Firm* — Westerman, Hattori, Daniels & Adrian, LLP

(57) ABSTRACT

A thermal treatment apparatus having a first light source emitting a first light having light diffusion property, a reflectance measuring unit irradiating a treatment target with the light from plural directions by the first light source and determining a light reflectance of the treatment target, a light irradiation controller adjusting an intensity of a second light of a second light source on the basis of the light reflectance, the second light has diffusion property, and a thermal treatment unit irradiating the treatment target with the second light having adjusted the intensity of the second light by the light irradiation controller.

13 Claims, 14 Drawing Sheets

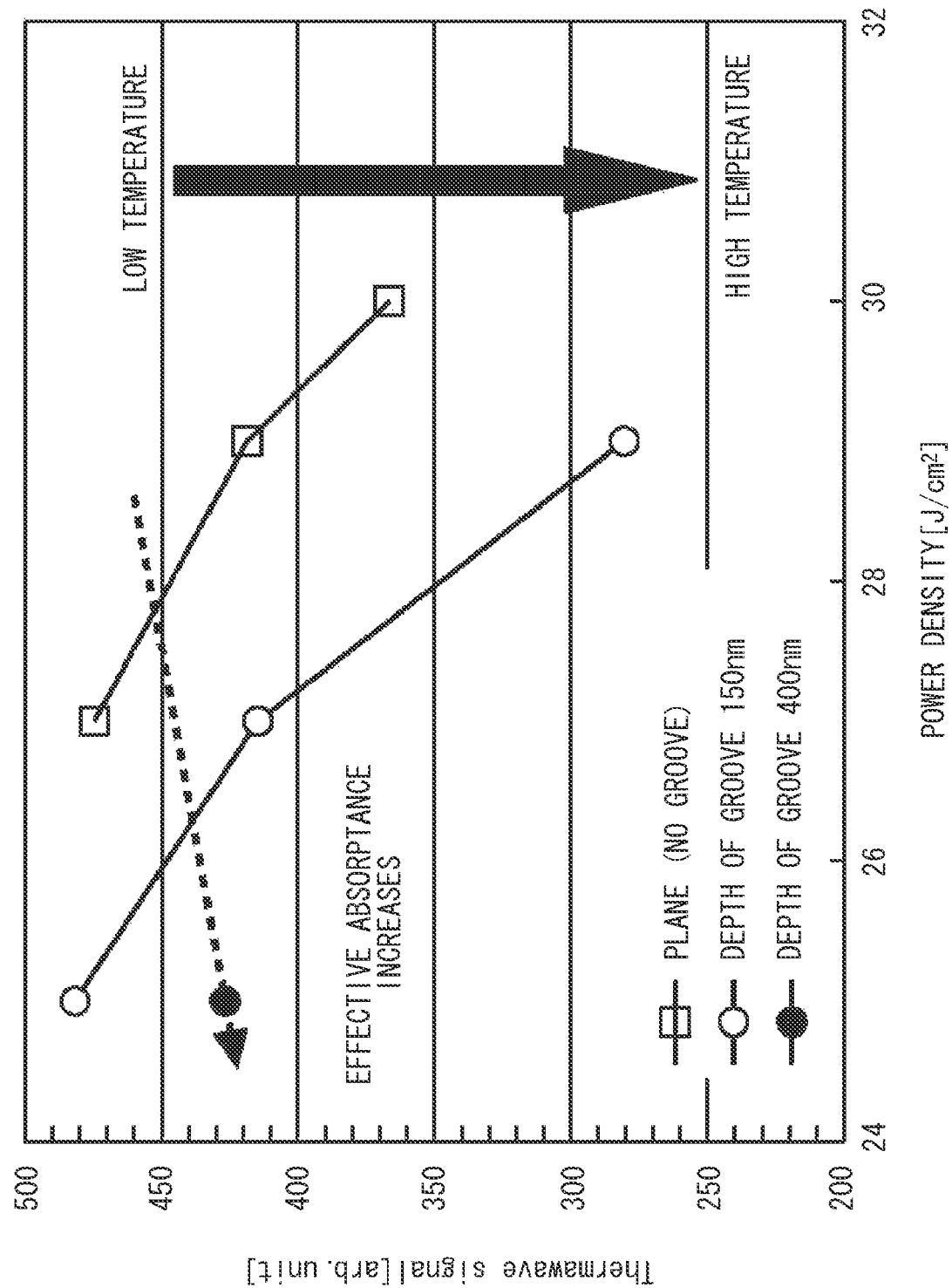

THERMAL TREATMENT APPARATUS, THERMAL TREATMENT METHOD AND METHOD OF MANUFACTURING SEMICONDUCTOR DEVICE

CROSS-REFERENCE TO RELATED APPLICATIONS

This application is based upon and claims the benefit of priority from the prior Japanese Patent Application No. 2007-263720, filed on Oct. 9, 2007, the entire contents of which are incorporated herein by reference.

TECHNICAL FIELD

The present invention relates to thermal treatment apparatus and method for performing a thermal treatment on a treatment target by light irradiation, and a semiconductor device manufacturing method containing an annealing treatment for activating impurities doped into a semiconductor substrate.

BACKGROUND

Miniaturization of transistors has been developing to continually improve performance of transistors. Furthermore, it has also been adopted to reduce parasitic resistance in an extension area which is formed to be superposed on a source/drain region. In order to implement the reduction of the parasitic resistance, it is necessary to form the extension area so that the extension area is shallow and has low resistance and the concentration profile of impurities (dopant) is steep.

In order to activate impurities doped in a semiconductor substrate, an annealing treatment is performed on the semiconductor substrate. Rapid Thermal Annealing (RTA) of about 10 seconds in treatment time is used as the annealing treatment of the extension area. When RTA is used, thermal diffusion occurs in the doped impurities, and the junction of the extension area is formed deeply. In order to suppress the thermal diffusion, it is necessary to suppress the annealing temperature to a low value. However, when the annealing temperature is set to a low value, the activation rate of the impurities is lowered, and thus the sheet resistance increases.

Furthermore, Spike Annealing having a treatment time of about 0.1 second to 1 second and annealing treatments such as Flash Lamp Annealing and Laser Annealing which can heat a treatment target to a temperature larger than 1200° C. for an extremely short treatment time of about 1 m second (hereinafter referred to as msec annealing treatments) are known.

The semiconductor substrate is subjected to the above annealing treatment after a predetermined pattern is formed on the surface of the semiconductor substrate. Accordingly, the effective absorptance of energy is varied in accordance with the pattern due to light refraction, light reflection, etc. which are caused by the pattern. Therefore, when the surface state of the semiconductor substrate is different, the semiconductor substrate is not set to the same temperature even if the surface of the semiconductor substrate is irradiated with light having the same energy.

Therefore, there is disclosed a technique of calculating light reflectance of the surface of the semiconductor substrate as the treatment target prior to the annealing treatment, and controlling light irradiation of the annealing treatment by using the calculated reflectance (for example, see Japanese Laid-open Patent Publication Nos. 2007-13047, 2005-39213, 2005-207997). In Japanese Laid-open Patent Publication Nos. 2007-13047 and 2005-39213, when the light reflectance of the surface of the semiconductor substrate is calculated, only reflection light vertical to the surface concerned is detected. Furthermore, in Japanese Laid-open Patent Publication No. 2005-207997, when the light reflectance of the surface of the semiconductor substrate is calculated, only reflection light of a predetermined angle which corresponds to irradiation light of a predetermined angle to the surface concerned is detected. The irradiation light of a light source used for the annealing treatment is not collimated light, but light having a wide angle component.

SUMMARY

A thermal treatment apparatus according to an aspect of the present invention includes a first light source emitting a first light a having light diffusion property, a reflectance measuring unit irradiating a treatment target with the light from plural directions by the first light source and determining a light reflectance of the treatment target, a light irradiation controller adjusting an intensity of a second light of a second light source on the basis of the light reflectance, the second light has a diffusion property, and a thermal treatment unit irradiating the treatment target with the second light having adjusted the intensity of the second light by the light irradiation controller.

BRIEF DESCRIPTION OF THE DRAWINGS

FIG. 3 is a characteristic chart showing a relationship between an energy density of irradiation light and a thermawave signal when the groove depth of the substrate is varied in a flash lamp annealing treatment;

DETAILED DESCRIPTION OF THE EMBODIMENTS

Accurate light reflectance which properly corresponds to the semiconductor substrate on which various patterns are formed cannot be obtained by detecting only one-way reflection light as in the case of the conventional technique.

The inventor of this application has studied the effective light absorptance of irradiation light in spike annealing treatment and msec annealing treatments (such as, laser annealing treatment, flash lamp annealing treatment, etc.).

For convenience of description, the effective light absorptance is referred to as effective absorptance. The determination of the effective absorptance is equivalent to the determination of effective light reflectance (hereinafter referred to as effective reflectance).

Figure 1:
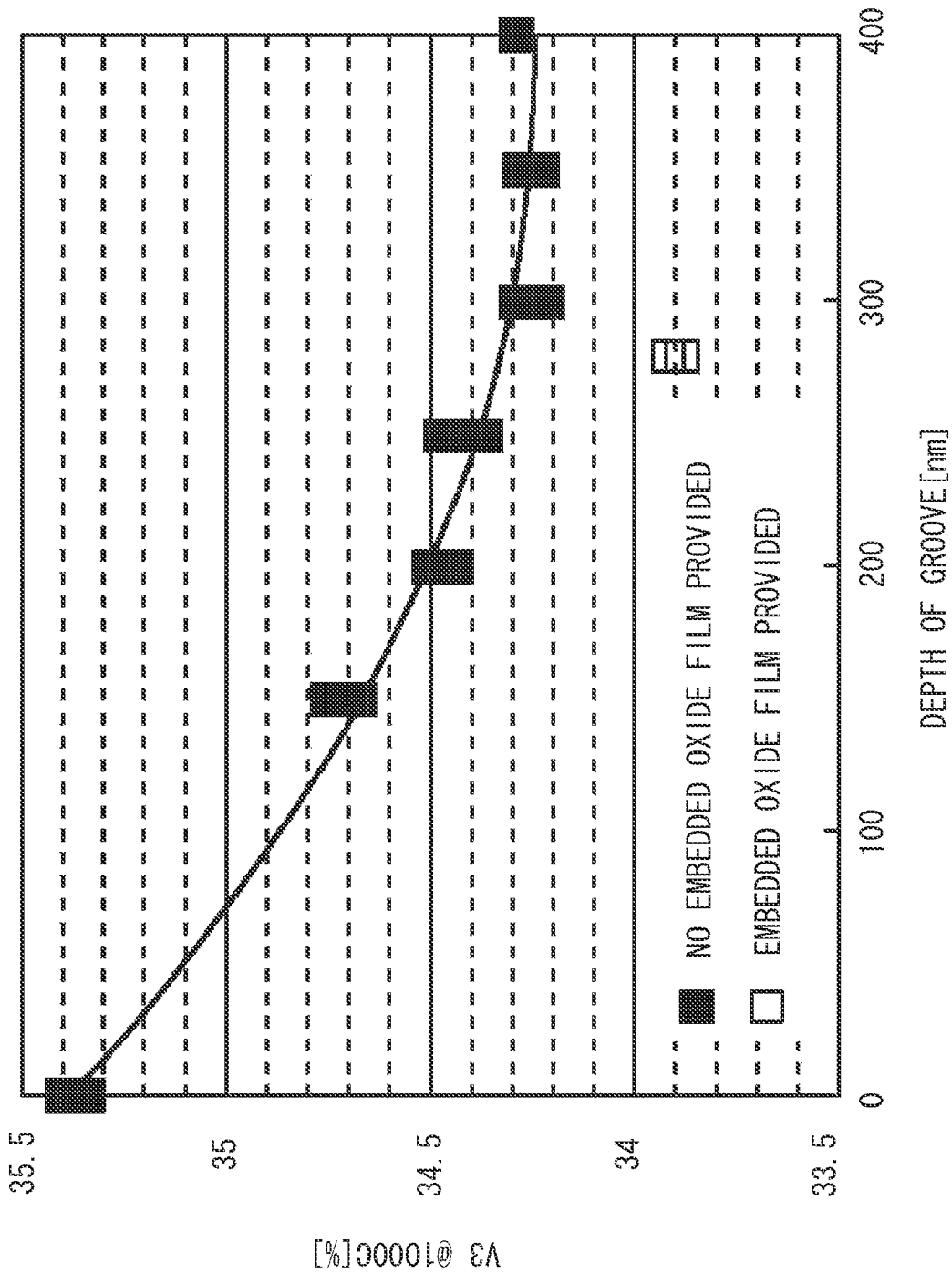
FIG. 1 is a characteristic chart showing a relationship between a groove depth of a substrate and an energy of irradiation light required to keep the temperature of the substrate at 1000° C. in a rapid thermal annealing treatment based on light irradiation.
Figure 2:
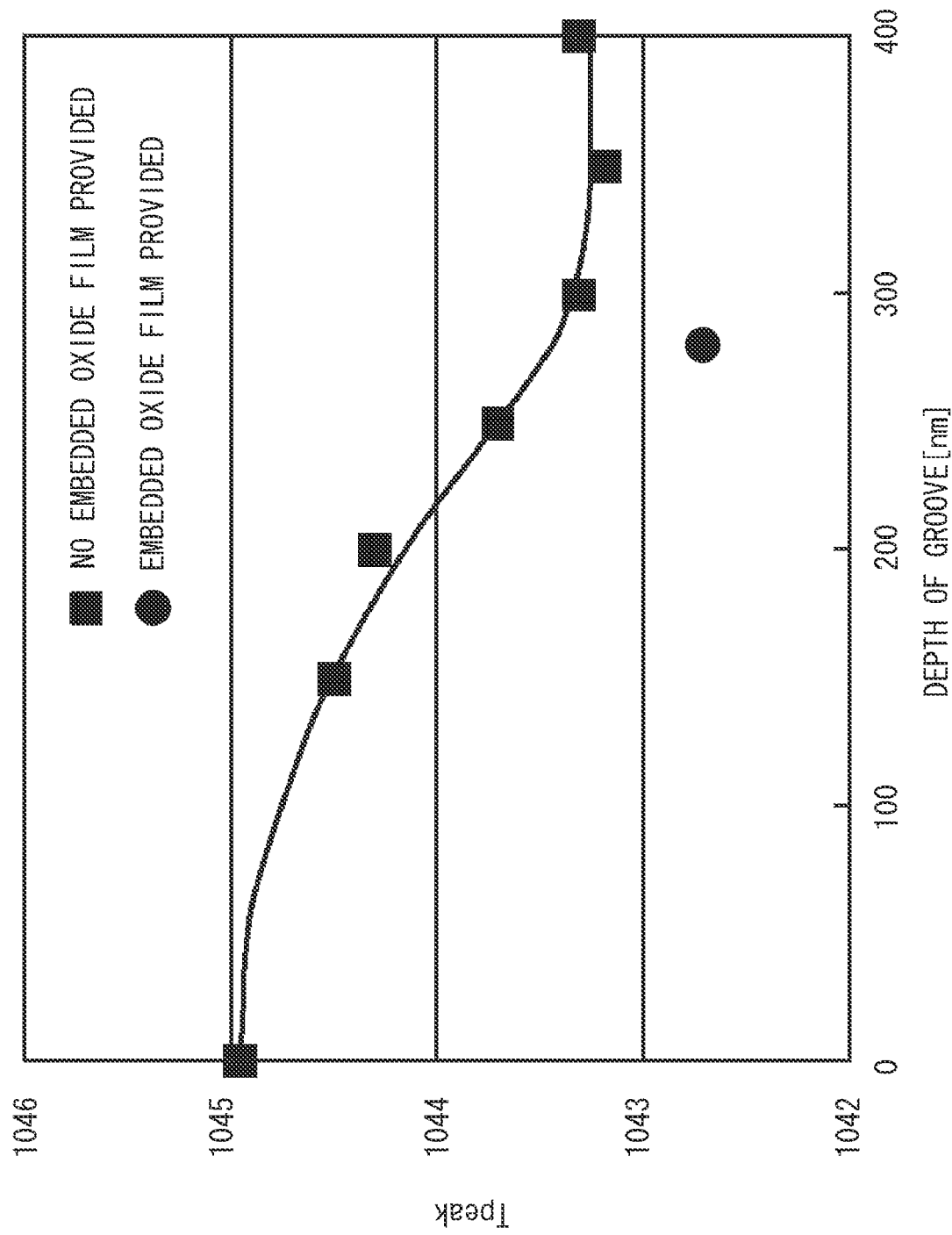
FIG. 2 is a characteristic chart showing a relationship between the groove depth of the substrate and a peak temperature of the substrate in the spike annealing treatment.

A surface state of a semiconductor substrate will be described by exemplifying a case where a groove (a separation groove filled with insulating material by an STI element separation method, for example) are formed on the surface of the semiconductor substrate. FIG. 1 shows an energy of irradiation light (lamp power) required to keep a temperature of the semiconductor substrate at a predetermined temperature (for example, 1000° C.) when the depth of the groove is varied from 0 nm to 400 nm. FIG. 2 shows a peak temperature of the semiconductor substrate in the spike annealing treatment when the groove depth is varied from 0 nm to 400 nm.

As shown in FIG. 1, as the groove is deeper, the lamp power required to maintain the temperature of the semiconductor substrate at 1000° C. decreases. This means that as the groove is deeper, the effective absorptance of irradiation light in the semiconductor substrate is larger (the effective reflectance is smaller).

As shown in FIG. 2, it is found that the peak temperature of the semiconductor substrate in the spike annealing treatment is lower as the groove is deeper. This means that the peak temperature of the semiconductor substrate in the spike annealing treatment is varied when the effective absorptance (effective reflectance) of irradiation light is varied because of the groove depth on the surface of the semiconductor substrate.

Next, FIG. 3 shows the relationship between an energy (power) density of irradiation light and Thermawave Signal when a depth of the groove on the surface of the semiconductor substrate is set to 0 (blanket substrate), 150 nm and 400 nm. Here, FIG. 3 shows the thermawave signal in the range of 5 μm×10 μm of a semiconductor substrate in which areas each of which is surrounded by a groove of 150 nm, 400 nm in depth and designed to be 1 μm×1 μm in plan view (i.e., each side of the area is set to 1 μm) are arranged in a lattice pattern.

Specifically, after grooves of 0 nm (no groove), 150 nm, 400 nm in depth are formed on the surface of the semiconductor substrate, ion implantation is conducted to form damage on the whole surface. Then, the flash lamp annealing treatment is executed, and a residual damage amount is measured by thermawave. From the measurement result, it is found that as the temperature of the surface of the semiconductor substrate is higher, the residual damage of the ion implantation is recovered and thus the thermawave signal is smaller. Here, it is also found that as the groove is deeper, the ion implantation damage is recovered even when the power density of light irradiation is lower in the flash lamp annealing treatment. That is, the effective absorptance is increased. With respect to the blanket substrate, the effective absorptance is increased by 1.08 time when the groove depth is set to 150 nm and increased by 1.15 time when the groove depth is set to 400 nm.

As described above, the variation of the effective absorptance of irradiation light in the annealing treatment in accordance with the surface state of the semiconductor substrate may be caused by the following factor.

Figure 4A:
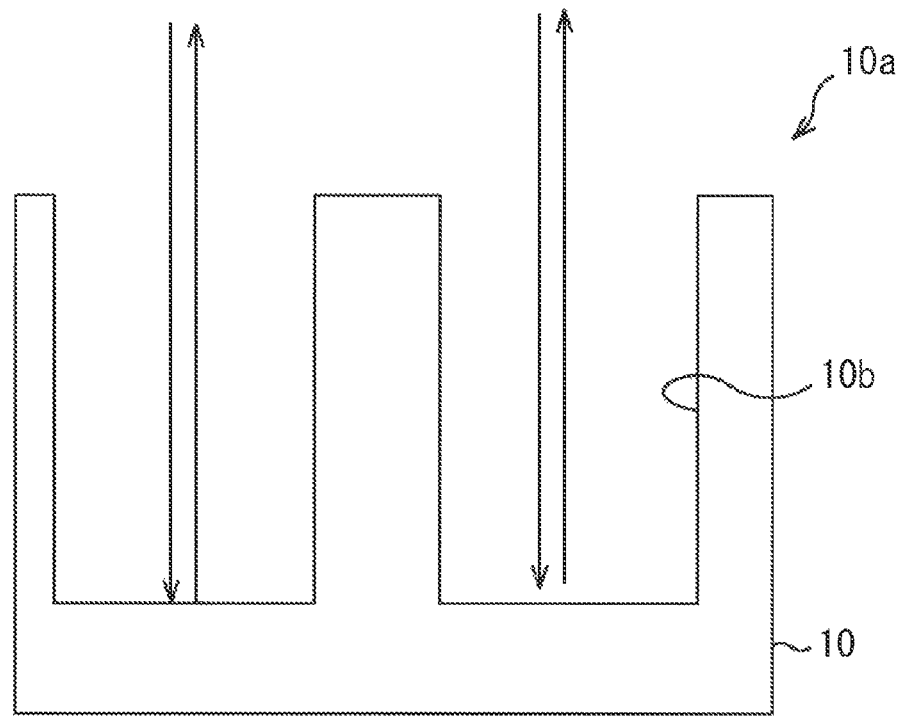
FIGS. 4A and 4B are schematic diagrams showing an effective absorptance when grooves of the substrate are formed.
Figure 4B:
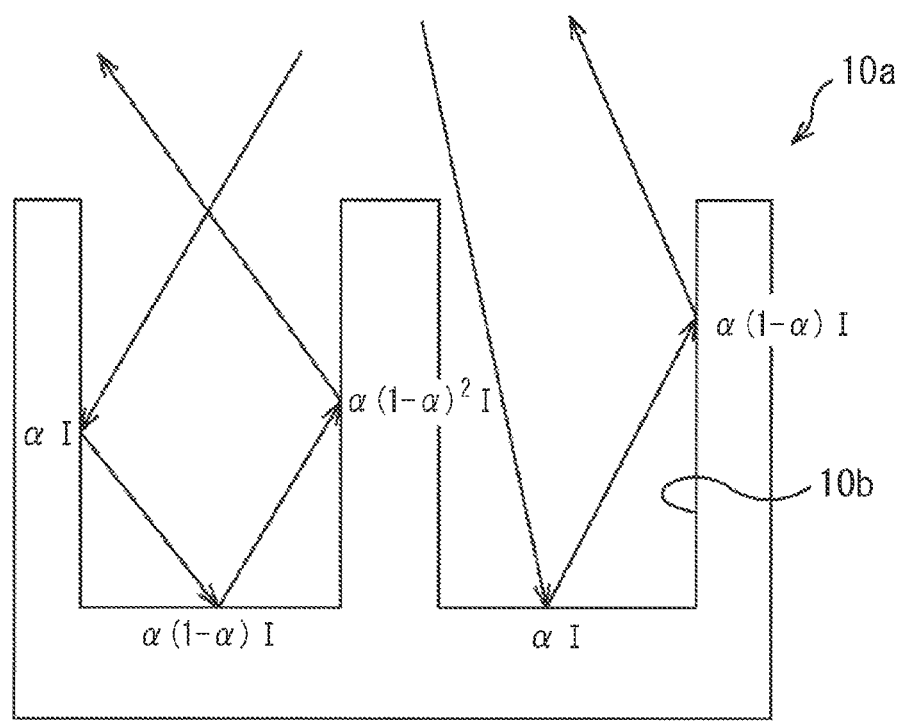

For example, in a case where collimated light such as a laser beam is irradiated to the surface 10a of a semiconductor substrate 10 in the vertical direction as shown in FIG. 4A, the effective absorptance of irradiation light hardly varies even when grooves 10b are formed on the surface 10a of the semiconductor substrate 10.

On the other hand, in a case where light having light diffusion property such as light from a halogen lamp of tungsten or a flash lamp (in this specification, it is called non-collimated light in comparison with collimated light such as laser beam or the like) is irradiated to the surface 10b of the semiconductor substrate 10, when the grooves 10b are formed on the surface 10a of the semiconductor substrate 10, the irradiation light is irradiated to the surface 10a from various directions, and thus the effective absorptance increases in proportion to the frequency of light reflection from the inner wall surfaces of the grooves 10b. For example, when the absorptance of irradiation light at the inner wall surface is represented by α, the effective absorptance increases in accordance with the light reflection frequency in the grooves 10b as follows:

$$\alpha+\alpha(1-\alpha)+\alpha(1-\alpha)^2+$$

As described above, when light having light diffusion property is used in the annealing treatment, the effective absorptance could not be accurately grasped if attention is paid to only the light irradiation in the vertical direction to the surface of the semiconductor substrate. This is the same if only the light irradiation of a predetermined angle to the surface of the semiconductor substrate is considered.

As described above, in the semiconductor substrate annealing treatment using the light source of light having light diffusion property such as a halogen lamp or a flash lamp, the effective absorptance (effective reflectance) of irradiation light in the annealing treatment varies greatly in accordance with the surface state of the semiconductor substrate. In connection with this variation, the peak temperature of the semiconductor substrate in the annealing treatment also varies. Accordingly, when the light reflectance of the surface of the semiconductor substrate is obtained to make the light irradiation proper in the annealing treatment, accurate light absorptance (light reflectance) which properly corresponds to the semiconductor substrate on which various patterns are formed cannot be obtained by detecting only the reflection light in one direction.

From the above fact, the inventor of this application has concluded that the angle distribution of the intensity of light having light diffusion property is required to be grasped in order to accurately determine the effective absorptance (effective reflectance) on the surface of the semiconductor substrate.

Here, when the direction vertical to the surface of the semiconductor substrate is set as a reference (the distance from the light source to the surface concerned at this time is represented by L and the intensity component of the irradiation light is represented by I0), the intensity component I(θ) of the irradiation light for an incident angle of θ is represented by the following equation (1):

$$I(\theta) = I0\cos\theta/4\pi(L/\cos\theta)^2 \quad (1)$$
$$= (I0/4\pi L^2) \cdot (\cos\theta)^3$$

Figure 5A:
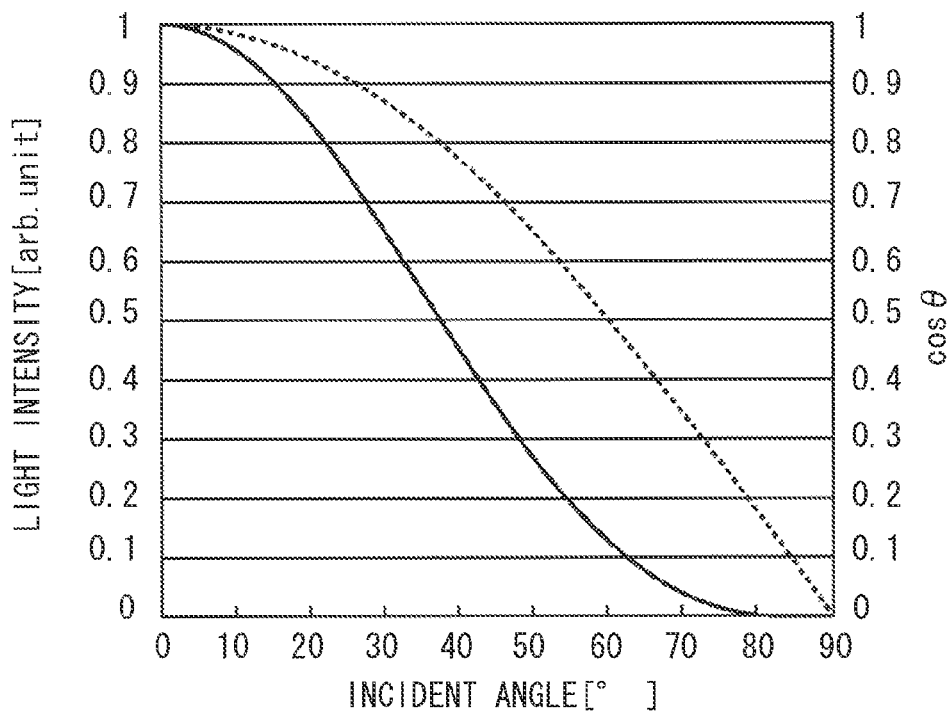
FIGS. 5A and 5B are characteristic charts showing an angle distribution of irradiation light intensity.
Figure 5B:
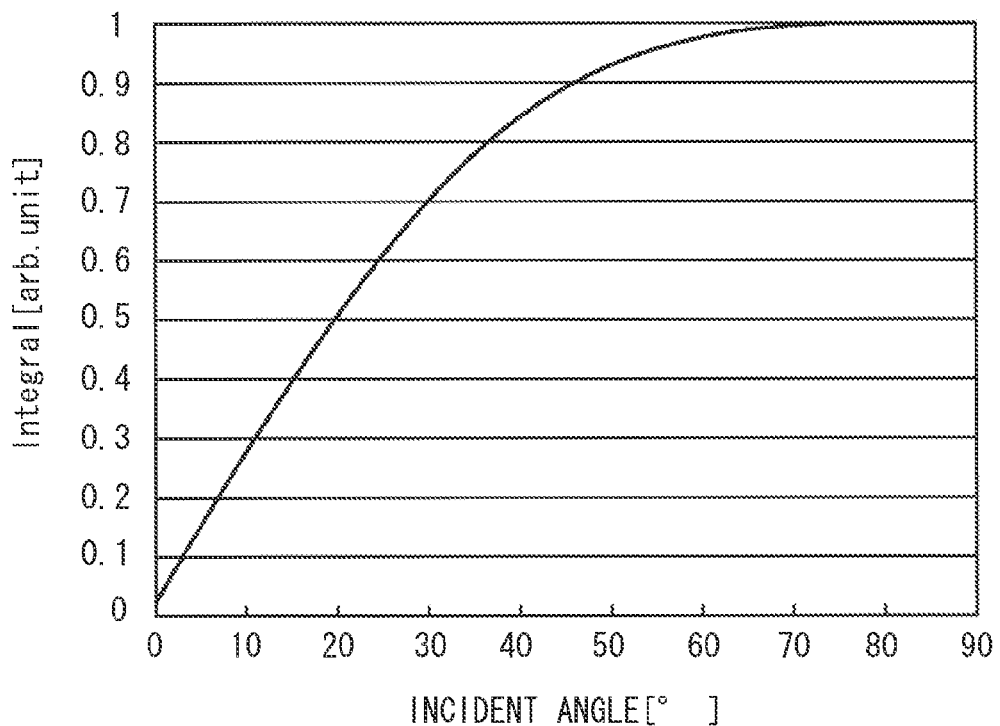

FIG. 5A shows the relationship between the incident angle θ and the intensity component of the irradiation light (and cos θ) at this time. FIG. 5B shows the rate of the integral value of the irradiation intensity from the vertical direction (θ=0) to some angle θ to the integration value of the irradiation intensity over the entire angle.

According to the present invention, in order to accurately determine the effective absorptance (effective reflectance) on the surface of the semiconductor substrate, an angle distribution of irradiation light intensity (angle intensity distribution) based on a first light source used to calculate the effective absorptance (detect reflection light) is adapted to an angle intensity distribution based on a second light source used in the annealing treatment (for example, FIG. 5A). It is preferable that a light source having the same light irradiation function as the second light source is used as the first light source, or a light source whose irradiation-light wavelength band is equal to the irradiation-light wavelength band of the second light source is used.

By making the first light source similar to the second light source, the light reflectance on the surface of the semiconductor substrate which is dependent on the light intensity distribution to the light irradiation angle of the irradiation light of the first light source, that is, the effective reflectance is determined. By adopting this construction, the accurate effective reflectance which properly corresponds to semiconductor substrates having various patterns formed thereon can be obtained.

Furthermore, according to the present invention, the irradiation light intensity (irradiation light energy) of the second light source is controlled so as to heat the surface of the semiconductor substrate to a desired temperature on the basis of the thus-determined effective reflectance of the surface of the semiconductor substrate without being dependent on the pattern formed on the surface. By adopting this construction, the peak temperature of the semiconductor substrate in the annealing treatment can be kept to a desired constant temperature even when the effective reflectance varies in accordance with the pattern formed on the surface of the semiconductor substrate.

First Embodiment

Figure 6:
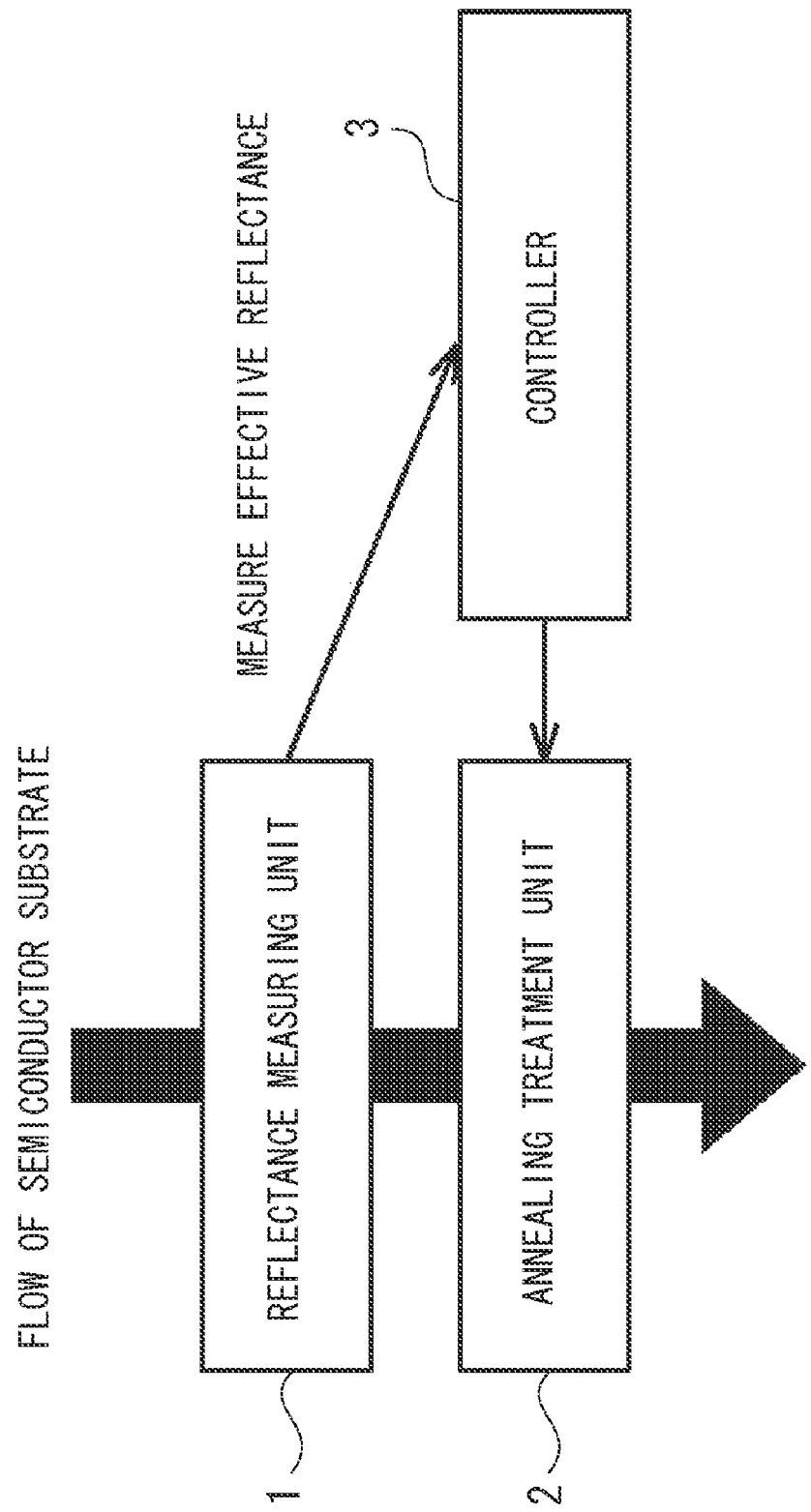
FIG. 6 is a block diagram showing a thermal treatment apparatus according to a first embodiment.

FIG. 6 is a block diagram showing the construction of a thermal treatment apparatus according to a first embodiment.

The thermal treatment apparatus contains a reflectance measuring unit 1, an annealing treatment unit 2 and a controller 3.

The reflectance measuring unit 1 has a first light source, and irradiates the surface of a treatment target (for example, a semiconductor substrate) with light from the first light source to determine the effective reflectance of the surface of the semiconductor substrate. The annealing treatment unit 2 has a second light source, and irradiates the surface of the semiconductor substrate with light from the second light source to conduct a thermal treatment on the surface of the semiconductor substrate. The controller 3 controls the irradiation light intensity (irradiation light energy) of the second light source in the annealing treatment unit 2 on the basis of the effective reflectance of the surface of the semiconductor substrate determined by the reflectance measuring unit 1.

Figure 7:
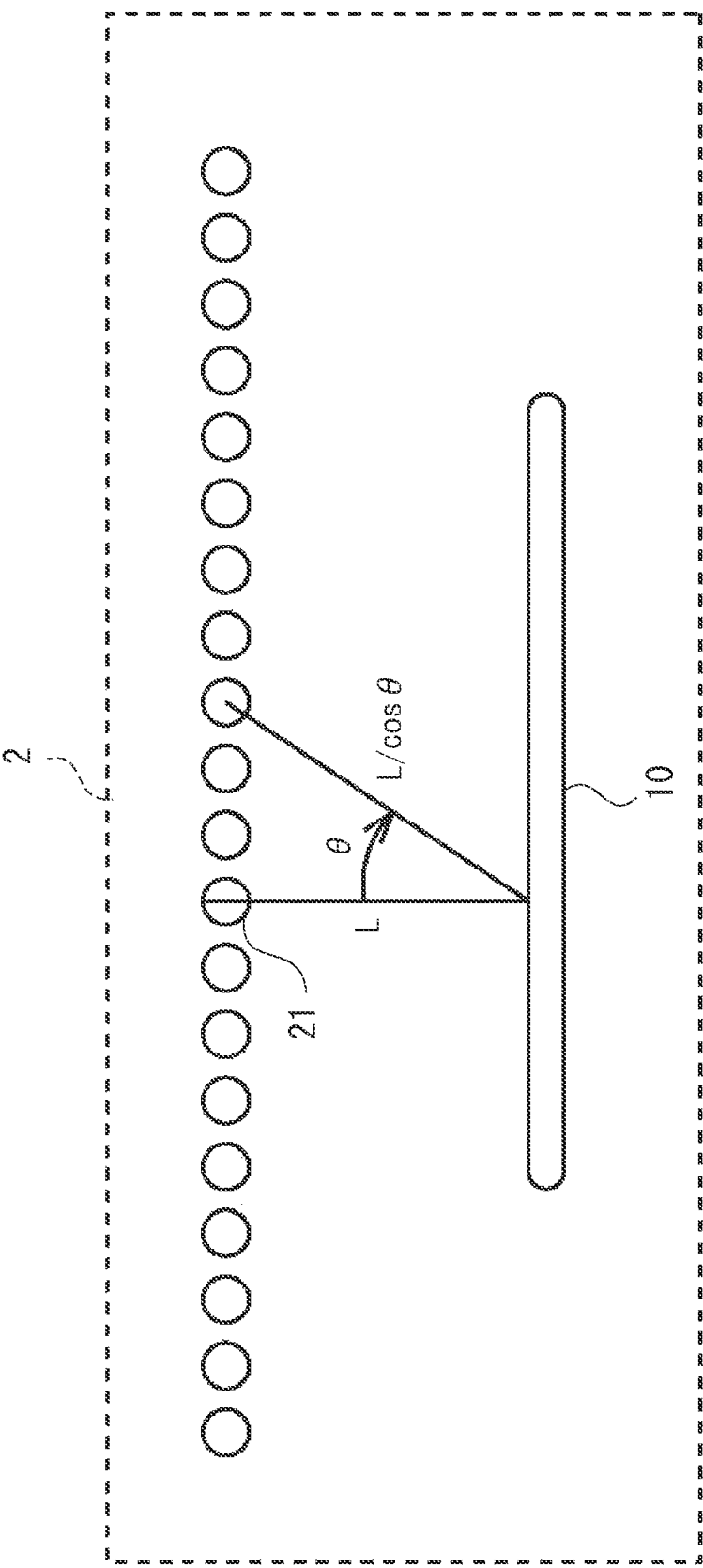
FIG. 7 is a schematic diagram showing an annealing treatment unit in the first embodiment.

In the annealing treatment unit 2, the semiconductor substrate 10 is disposed so as to face to the second light source 21 as show in FIG. 7 in a treatment chamber (not shown). A tungsten lamp is used as the second light source 21 for RTA or spike annealing. An Xe flash lamp or an Ar flash lamp is used for msec annealing. The second light source 21 is a lamp for emitting irradiation light having a broad angle distribution. In the second light source 21, the intensity component I(θ) of the irradiation light for an incident angle θ is represented by the above equation (1).

Figure 8:
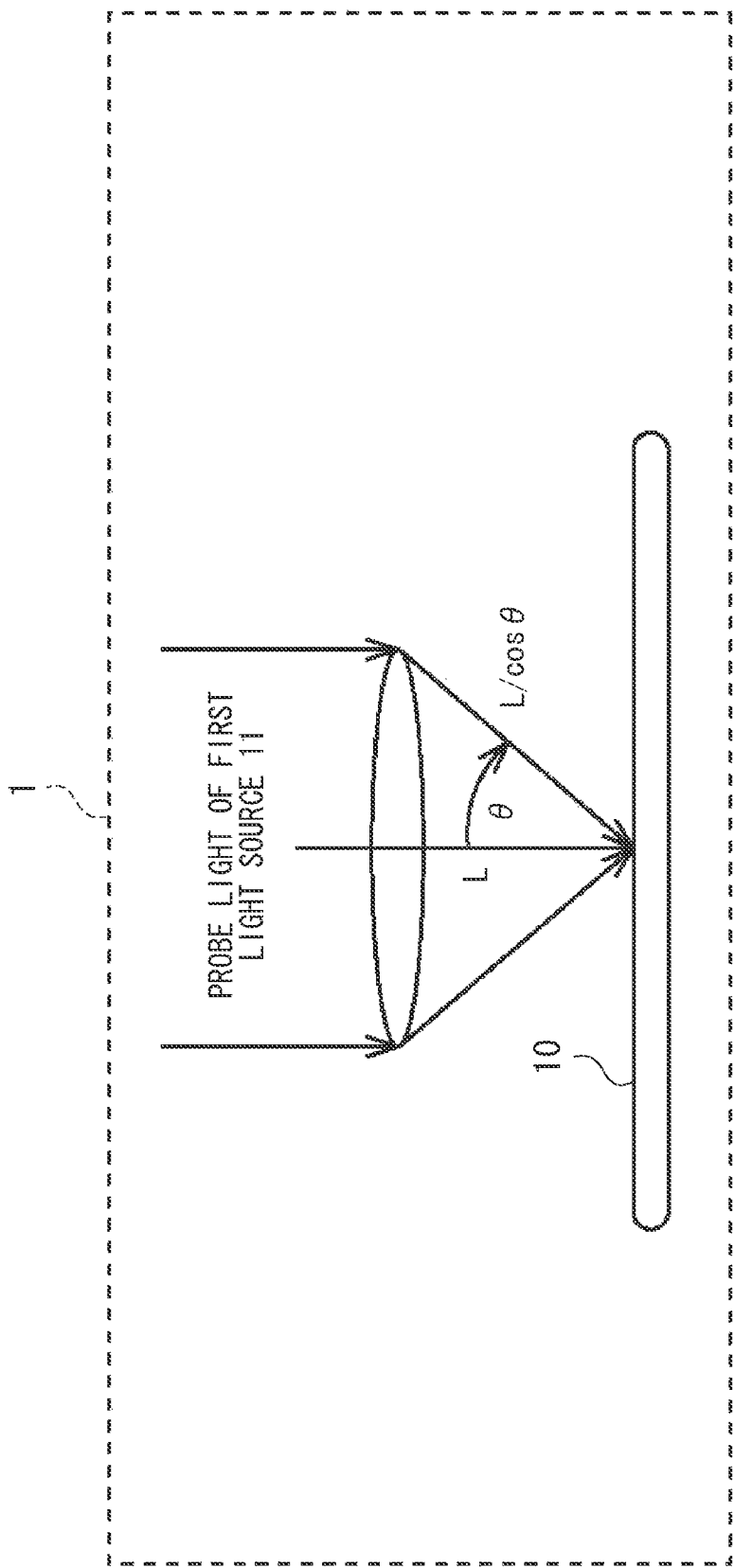
FIG. 8 is a schematic diagram showing a reflectance measuring unit in the first embodiment.
Figure 9:
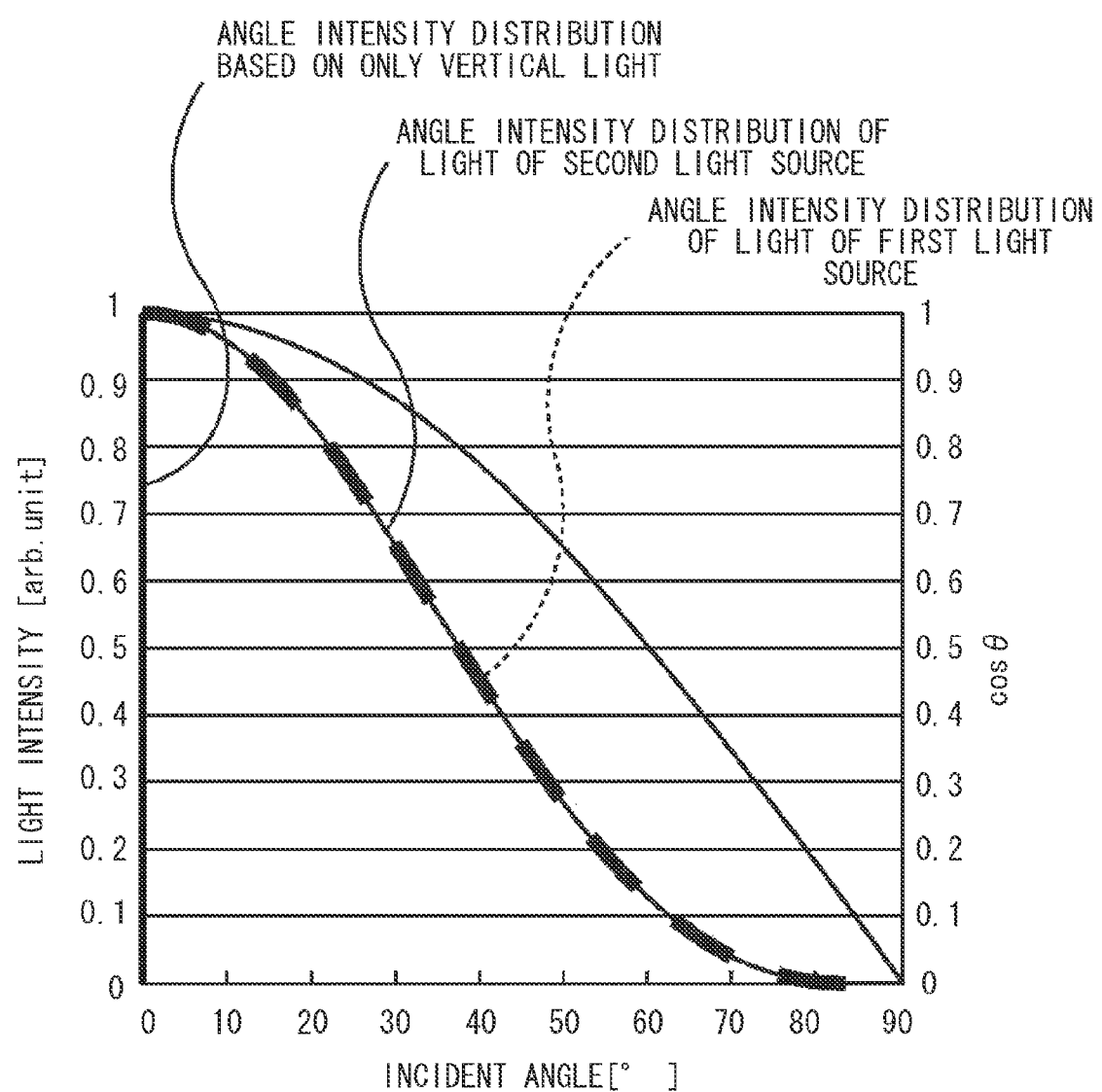
FIG. 9 is a characteristic charts showing an angle intensity distribution of irradiation light in each light source of the annealing treatment unit and the reflectance measuring unit.

In the reflectance measuring unit 1, the semiconductor substrate 10 is disposed so as to face the first light source 11 as shown in FIG. 8. The intensity component I(θ) of irradiation light represented by the equation (1) is equally set in first light source 11. That is, as shown in FIG. 9, the angle intensity distribution of the irradiation light is set so as to be substantially equal to the angle intensity distribution of the irradiation light of the second light source 21. In this case, a lamp having the same light irradiation function (the same type light source) as the second light source 21 or a lamp having the same irradiation-light wavelength band as the second light source 21 is used as the first light source 11. For reference, FIG. 9 shows the angle intensity distribution of light for reflectance measuring light irradiated from the vertical direction to the surface of the semiconductor substrate.

A light source for emitting light having a broader emission spectrum than the second light source 21 may be used as the first light source 11. In this case, it is preferable to measure light reflectance at each wavelength, weight the measured light reflectance by the emission spectrum of the second light source 21 and the integrate (average) the weighted reflectance.

Figure 10:
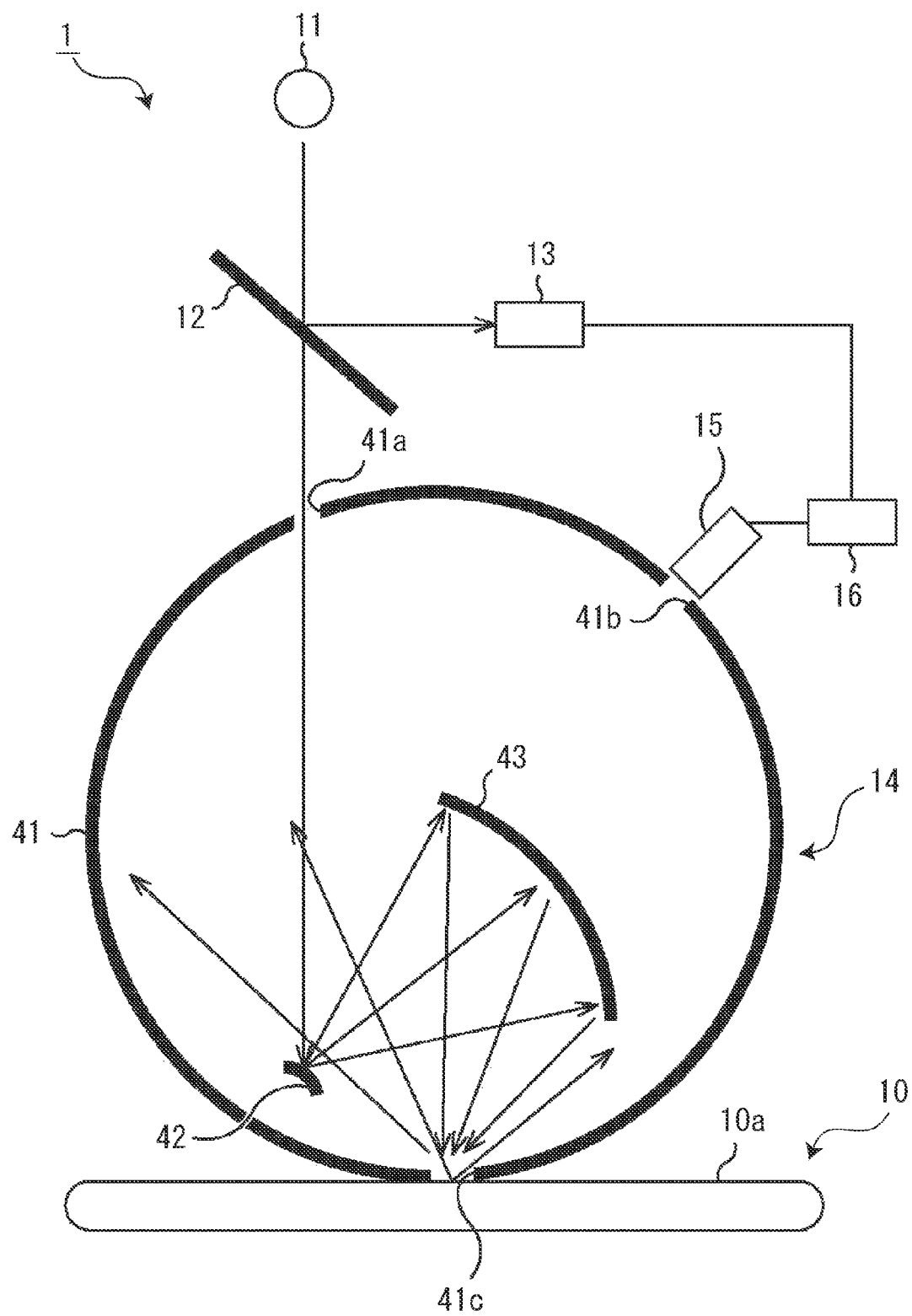
FIG. 10 is a schematic diagram showing the reflectance measuring unit in the first embodiment.

As shown in FIG. 10, the reflectance measuring unit 1 contains the first light source 11, a half mirror 12, an incident light sensor 13 for measuring the intensity of irradiation light of the first light source 11 which is reflected from the half mirror 12, an integrating sphere mechanism 14, a diffuse reflection light sensor 15 that is provided at the emission port of the integrating sphere mechanism 14 to determine the intensity of the reflection light, and an effective reflectance calculator 16 for calculating effective reflectance of the surface of the semiconductor substrate 10 on the basis of the reflection light intensity determined in the diffuse reflection optical sensor 15 and the irradiation light intensity determined by the incident light optical sensor 13. The first light source 11, the half mirror 12 and the incident light sensor 13 constitute an incident light measuring unit.

The integral sphere mechanism 14 is designed so that the inner surface thereof has a mirror structure and a surface thereof as a reflectance measurement target is rough, and it is used to monitor diffused reflection light. In the integral sphere mechanism 14, the light intensity of the whole surface of the inner wall can be determined by spatially integrating the diffused reflection light. If the emission port of light is sufficiently smaller than the size of the integral sphere, a uniform intensity distribution proportion to the light intensity of the light source is obtained at the emission port face as in the case of the other places, and thus the diffuse reflectance of the measurement target can be accurately measured.

The integral sphere mechanism 14 contains a spherical shell 41 whose inner surface is a mirror construct. The spherical shell 41 contains an incident port 41a, an emission port 41b, and an opening 41c through which light is irradiated to the surface of the semiconductor substrate 10. A convex mirror 42 and a concave mirror 43 are provided in the spherical shell 41. This construction makes it possible to irradiate the opening 41c with light from plural directions. The convex mirror 42 and the concave mirror 43 is preferably disposed so as to be positionally adjusted so that the angle intensity distribution of the first light source 11 is coincident with the angle intensity distribution of the irradiation light of the second light source 21 in the annealing treatment unit 2.

The reflectance measuring unit 1 makes the irradiation light from the first light source 11 incident to the half mirror 12. The half mirror 12 reflects the incident light to the incident light sensor 13. The incident light sensor 13 detects the reflected light and determines the light intensity thereof.

The half mirror 12 transmits the incident light therethrough. The transmitted light is irradiated through the incident port 41a into the spherical shell 41, and temporarily expanded by the convex mirror 42. The expanded light is condensed by the concave mirror 43, passed through the opening 41c and then irradiated to the surface 10a of the semiconductor substrate 10. The light which is diffused and reflected from the surface 10a of the semiconductor substrate 10 is reflected in the spherical shell 41 to be made uniform, and the reflection light concerned is detected by the diffuse reflection light sensor 15. The light intensity of this reflection light is determined as light having the intensity proportional to the intensity of the whole reflection light by the diffuse reflection light sensor 15.

The effective reflection calculator 16 calculates the effective reflectance on the basis of the irradiation light intensity determined in the incident light sensor 13 and the reflection light intensity determined in the diffuse reflection light sensor 15 as follows. When the irradiation light intensity determined in the incident light sensor 13 is represented by I0, the reflection light intensity determined in the diffuse reflection light sensor 15 is represented by Ir and the constant of proportion determined in consideration of the light transmittance in the half mirror 12, etc. is represented by β, the effective reflectance reff is represented as follows:

$$\text{Reff} = \beta Ir/I0 \quad (2)$$

The controller 3 corrects the irradiation light energy of the second light source 21 in the annealing treatment unit 2 on the basis of the effective reflectance on the surface of the semiconductor substrate 10 calculated in the reflectance measuring unit 1 so as to keep the peak temperature of the semiconductor substrate 10 to a desired constant temperature. When the irradiation light energy of the second light source 21 before the correction is represented by E0, the corrected irradiation light energy E of the second light source 21 is represented as follows:

$$E = E0/(1-\text{reff})$$

Figure 11:
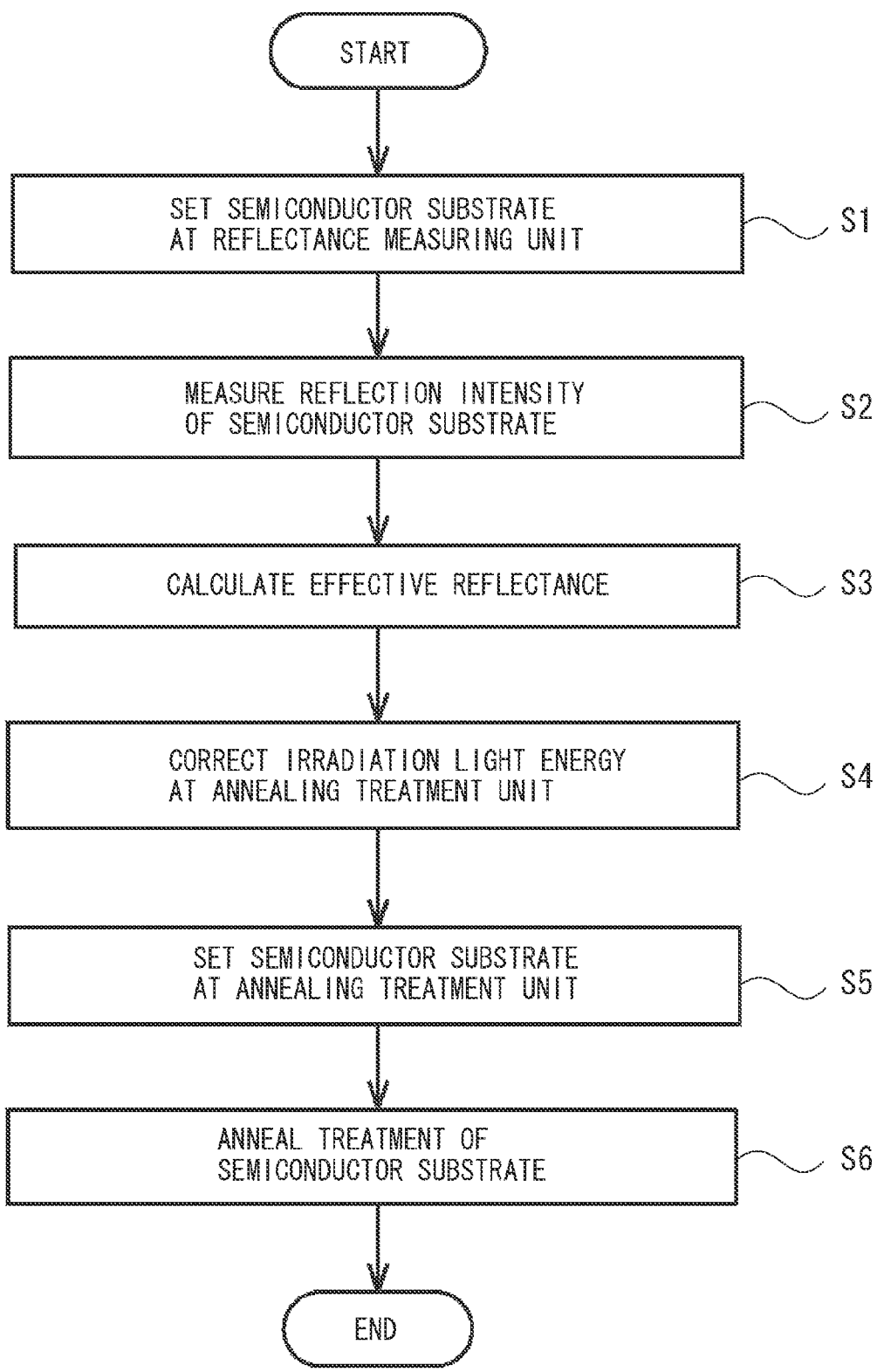
FIG. 11 is a flowchart showing an annealing treatment process of a semiconductor substrate which uses a thermal treatment apparatus in the first embodiment.

FIG. 11 is a diagram showing the annealing treatment process of the semiconductor substrate 10 which uses the thermal treatment apparatus described above.

First, the semiconductor substrate 10 is disposed in the reflectance measuring unit 1 so that a measuring portion on the surface thereof is exposed from the opening 41c of the spherical shell 41 of the integral sphere mechanism 14 (step S1).

Subsequently, the surface 10a of the semiconductor substrate 10 is irradiate with light from the first light source 11, and the light intensities are determined by the incident light sensor 13 and the diffuse reflection light sensor 15 (step S2).

Subsequently, the effective reflectance is calculated on the basis of each light intensity determined in step S2 by the effective reflectance calculator 16 (step S3).

Subsequently, on the basis of the effective reflectance calculated in step S3, the controller 3 corrects the irradiation light energy of the second light source 21 in the annealing treatment unit 2 so that the peak temperature of the semiconductor substrate 10 is kept to a desired constant temperature (step S4).

Subsequently, the semiconductor substrate 10 is disposed in the annealing treatment unit 2 (step S5).

The surface of the semiconductor substrate 10 is irradiated with irradiation light which is emitted from the second light source 21 and whose irradiation light energy is corrected and adjusted in step S4, thereby conducting the annealing treatment on the semiconductor substrate 10 (step S6).

As described above, according to the first embodiment, the accurate effective reflectance which properly corresponds to the semiconductor substrate on which various patterns are formed can be obtained. On the basis of the effective reflectance, the annealing treatment can be conducted so that the peak temperature of the semiconductor substrate can be kept to a desired value.

Modification

A modification of the first embodiment will be described hereunder. This modification is different from the first embodiment in the integral sphere mechanism of the reflectance measuring unit 1. The same constituent elements as the first embodiment are represented by the same reference numerals, and the description thereof is omitted.

Figure 12:
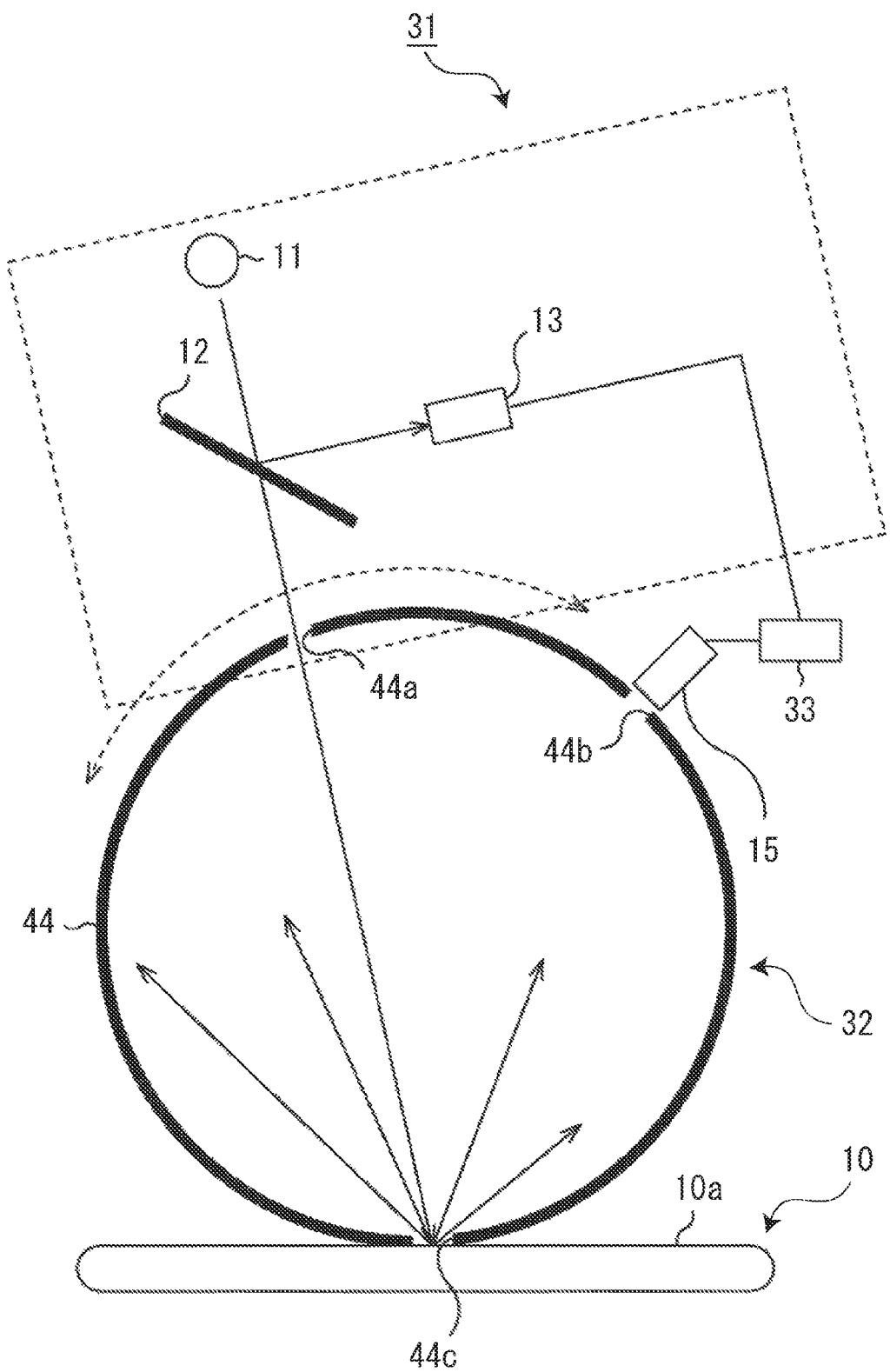
FIG. 12 is a schematic diagram showing a reflectance measuring unit according to a modification of the first embodiment.

FIG. 12 is a schematic diagram showing the construction of the reflectance measuring unit of the thermal treatment apparatus according to the modification of the first embodiment.

The reflectance measuring unit 31 is equipped with a first light source 11, a half mirror 12, an incident light sensor 13 for measuring the intensity of the irradiation light of the first light source 11 which is reflected from the half mirror 12, an integral sphere mechanism 32, a diffuse reflection light sensor 15 which is provided at the light emission port of the integral sphere mechanism 32 and determines the intensity of the irradiation light, and an effective reflectance calculator 33 for calculating the effective reflectance on the surface of the semiconductor substrate 10 on the basis of the irradiation light intensity determined from the incident light sensor 13 and the reflection light intensity of each incident angle which is determined from the diffuse reflection light sensor 15.

The integral sphere mechanism 32 contains a spherical shell 44 whose inner surface has a mirror construction. The spherical shell 44 contains an incident port 44a, an emission port 44b and an opening 44c through which the surface of the disposed semiconductor substrate 10 is irradiated with light. In the spherical shell 44, the incident port 44a is freely rotationally movable (swingable) interlockingly with the first light source 11, the half mirror 12 and the incident light sensor 13 (In FIG. 12, an incident light measuring unit surrounded by a broken line). Here, the swinging motion is made around the center position of the spherical shell 44. Furthermore, the emission port 44b, the opening 44c and the diffuse reflection light sensor 15 are positionally fixed, and these elements are unmovable even when the incident port 44a is swung.

First, the incident port 44a of the spherical shell 44, the first light source 11, the half mirror 12 and the incident light sensor 13 are turned and fixed to a predetermined incident angle.

In the reflectance measuring unit 31, the irradiation light from the first light source 11 is incident to the half mirror 12.

In the half mirror 12, the reflection light is detected by the incident light sensor 13, and the light intensity thereof is determined by the incident light sensor 13.

The light transmitted through the half mirror 12 is irradiated from the incident port 44a into the spherical shell 44 at the predetermined incident angle, passed through the opening 44c and then applied to the surface of the semiconductor substrate 10. The light which is diffused and reflected from the surface of the semiconductor substrate 10 is reflected in the spherical shell 44 to be made uniform, and the reflection light is detected by the diffuse reflection light sensor 15 to determine the light intensity.

The light intensity is determined for every incident angle by the diffuse reflection light sensor 15 while the incident angles of the incident port 44a of the spherical shell 44, the first light source 11, the half mirror 12 and the incident light sensor 13 are varied.

In the effective reflectance calculator 33, the diffuse reflectance of each incident angle is calculated by using the equation (2) of the first embodiment. When the irradiation light intensity at the incident angle θ determined in the incident light sensor 13 is represented by I0(θ), the reflectance light intensity at the incident angle θ determined in the diffuse reflection light sensor 15 is represented by Ir(θ) and the constant of proportion which is obtained in consideration of the light transmittance of the half mirror 12, etc. is represented by β, the diffuse reflectance r(θ) at the incident angle θ is represented as follows:

$$R(\theta) = \beta Ir(\theta)/I0(\theta) \quad (2)'$$

In the effective reflectance calculator 33, the diffuse reflectance of each incident angle is weighted by the angle intensity distribution of the irradiation light of the second light source 21 in the annealing treatment unit 2 and integrated (averaged) over the whole incident angle, whereby the effective reflectance is determined.

The controller 3 corrects the irradiation light energy of the second light source 21 in the annealing treatment unit 2 on the basis of the effective reflectance on the surface of the semiconductor substrate 10 calculated in the reflectance measuring unit 31 so that the peak temperature of the semiconductor substrate 10 is kept to a desired fixed temperature.

Figure 13:
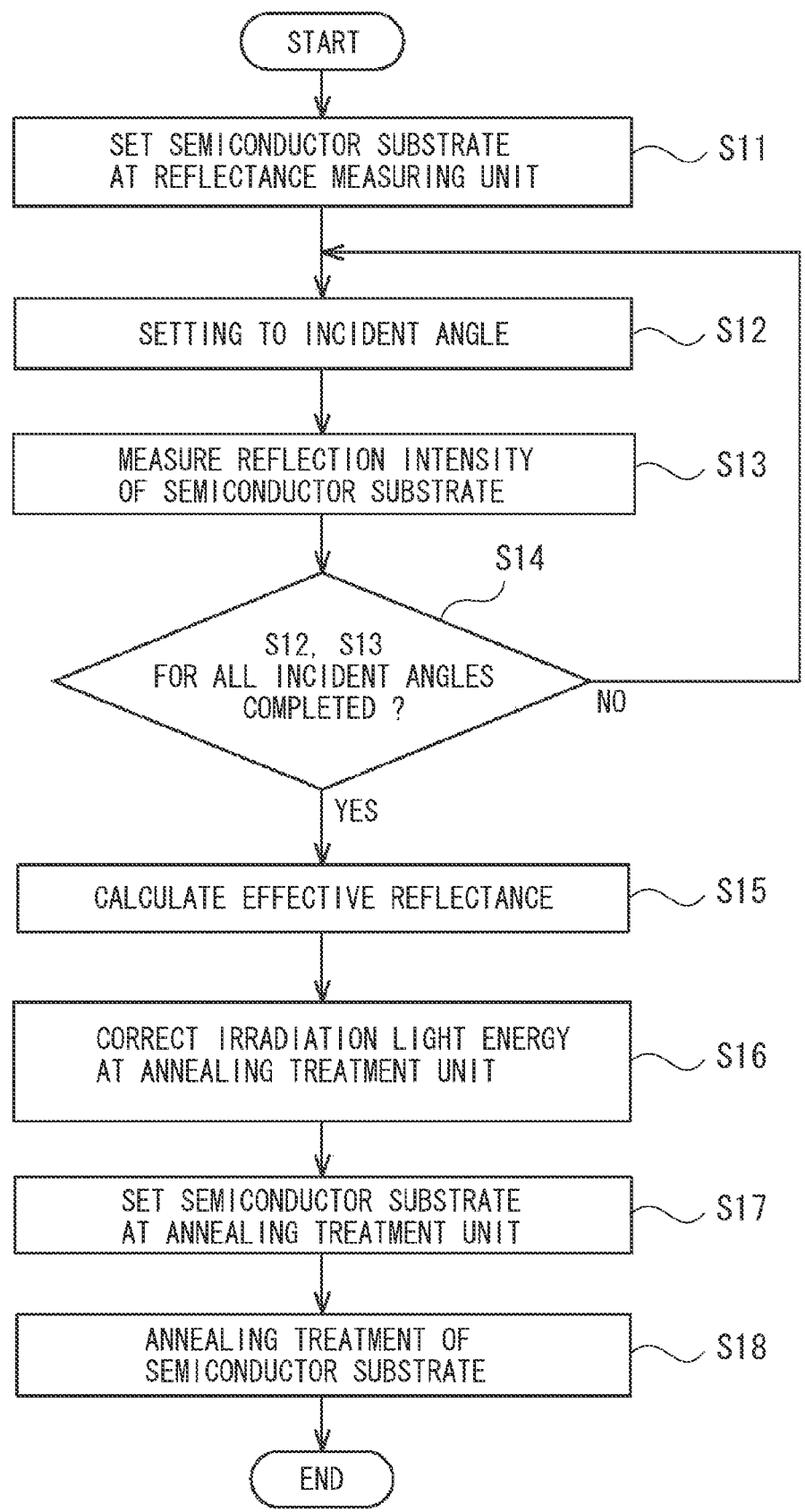
FIG. 13 is a flowchart showing an annealing treatment process of the semiconductor substrate which uses a thermal treatment apparatus of a modification of the first embodiment.

FIG. 13 shows the annealing treatment process of the semiconductor substrate 10 which uses the thermal treatment apparatus described above.

First, in the reflectance measuring unit 31, the semiconductor substrate 10 is disposed so that a measuring portion on the surface thereof is exposed from the opening 44c of the spherical shell 44 of the integral sphere mechanism 32 (step S11).

Subsequently, the incident port 44a of the spherical shell 44, the first light source 11, the half mirror 12 and the incident light sensor 13 are fixed to predetermined incident angles (step S12).

Subsequently, light is emitted from the first light source 11 and the light intensities are detected by the incident light sensor 13 and the diffuse reflection light sensor 15 (step S13).

The steps S12, S13 are repetitively executed for every incident angle (step S14).

Subsequently, the effective reflectance is calculated by the effective reflectance calculator 33 on the basis of the light intensity (each light intensity determined in the diffuse reflection light sensor 15) of each incident angle which is determined through the step S14 (step S15).

Subsequently, on the basis of the effective reflectance calculated in the step S15, the controller 3 corrects the irradiation light energy of the second light source 21 in the annealing treatment unit 2 so that the peak temperature of the semiconductor substrate 10 is kept to a desired fixed temperature (step S16).

Subsequently, the semiconductor substrate 10 is disposed in the annealing treatment unit 2 (step S17).

The surface of the semiconductor substrate 10 is irradiated with the irradiation light which is emitted from the second light source 21 and whose irradiation light energy is corrected and adjusted in step S4, thereby conducting the annealing treatment on the semiconductor substrate 10 (step S18).

As described above, the accurate effective reflectance which properly corresponds to the semiconductor substrate on which various patterns are formed can be obtained, and the annealing treatment in which the peak temperature of the semiconductor substrate can be kept to a desired value on the basis of the effective reflectance can be performed.

Second Embodiment

In this embodiment, a method of manufacturing a semiconductor device to which the annealing treatment of the first embodiment is applied will be described. In this embodiment, a method of manufacturing an MOS transistor will be described as an example. However, this embodiment is not limited to this example, and it may be applied to a semiconductor device having various kinds of semiconductor memories, etc. which needs a thermal process.

FIGS. 14A to 14F are cross-sectional views showing the process flow of the MOS transistor manufacturing method according to a second embodiment.

Figure 14A:
FIGS. 14A to 14F are cross-sectional views showing a method of manufacturing MOS transistor according to a second embodiment.

As shown in FIG. 14A, element separation structures 101 are formed on the surface of the semiconductor substrate 10 by an STI element separating method to thereby isolate active regions.

Figure 14B:
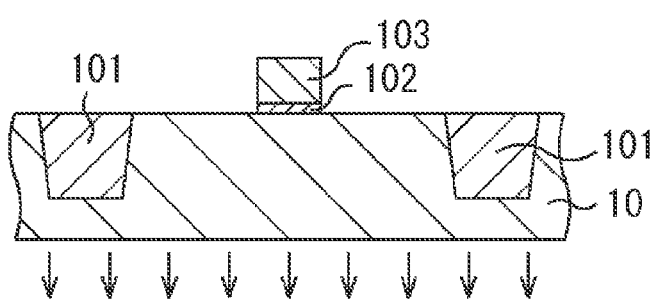

Subsequently, as shown in FIG. 14B, the surface of the semiconductor substrate 10 is thermally oxidized to form oxide film, and then polycrystalline silicon film (not shown) is deposited by the CVD method or the like. The polycrystalline silicon film and the oxide film are processed by lithography and dry etching to form a gate electrode 103 extending through gate insulating film 102 on the active region.

Figure 14C:
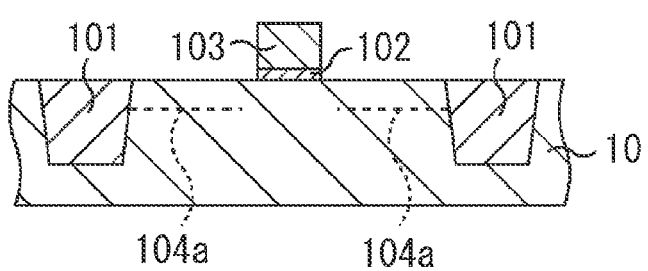

Subsequently, as shown in FIG. 14C, impurities 104a are ion-implanted into the active regions at both the sides of the gate electrode 103 by using the gate electrode 103 as a mask. Here, for example, boron (B+) is used as the impurities 104a when the MOS transistor to be formed is p-type, and arsenic (As+) is used when the MOS transistor to be formed is n-type. In the p-type case, ion implantation is carried out at a dose amount of $1 \times 10^{14}/cm^2$ to $2 \times 10^{15}/cm^2$ with acceleration energy of 1 keV or less. In the n-type case, ion implantation is carried out at a dose amount of $1 \times 10^{14}/cm^2$ to $2 \times 10^{15}/cm^2$ with acceleration energy of 0.5 keV to 5 keV.

Figure 14D:
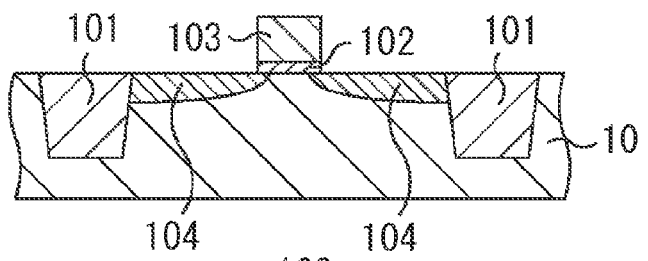

Subsequently, as shown in FIG. 14D, the surface of the semiconductor substrate 1 is heated for about 1 millisecond in treatment time by the annealing treatment shown in the first embodiment or the modification, particularly by the flash lamp annealing treatment in this case. By this annealing treatment, the impurities 104a doped into the active region are activated, and a pair of extension regions 104 which have low resistance, a steep concentration profile of the impurities and shallow junctions are formed.

Figure 14E:
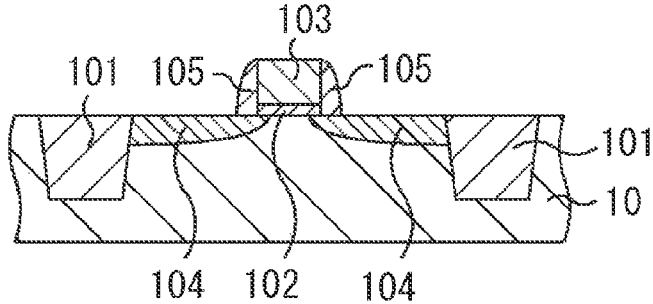

Subsequently, as shown in FIG. 14E, silicon oxide film is deposited on the whole surface containing the upper surface of the gate electrode 103, and the whole surface is subjected to anisotropic dry etching (etch back), whereby side wall insulating film 105 is formed while the silicon oxide film is left on both the side surfaces of the gate electrode 103.

Figure 14F:
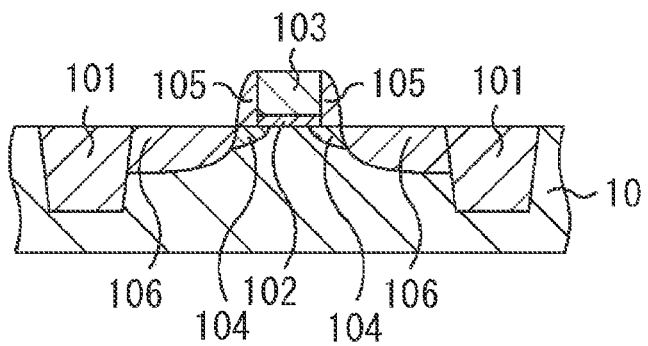

Subsequently, as shown in FIG. 14F, impurities are ion-implanted into the active regions at both sides of the gate electrode 103 by using the gate electrode 103 and the side wall insulating film 105 as masks. Here, for example, the impurities are boron (B+) when the MOS transistor to be formed is p-type, and phosphorus (P+) when the MOS transistor to be formed is n-type. In the p-type case, the ion implantation is carried out at a dose amount of $2\times10^{15}/cm^2$ to $1\times10^{16}/cm^2$ with acceleration energy of 2 keV to 5 keV. In the n-type case, the ion implantation is carried out at a dose amount of $2\times10^{15}/cm^2$ to $1\times10^{16}/cm^2$ with acceleration energy of 1 keV to 20 keV.

By conducting the annealing treatment on the surface of the semiconductor substrate 10, source/drain regions 106 which are partially overlapped with the extension regions 104 and have deeper junctions than the extension regions 104 are formed.

Thereafter, inter-layer insulating film, connection holes and various kinds of wires are formed, thereby completing the MOS transistor.

As described above, according to this embodiment, the extension regions 104 can be formed so that the resistance thereof is low, the concentration profile of impurities is steep and the junction state is shallow, and a high-performance and minute MOS transistor can be implemented.

In this embodiment, the thermal treatment method of the present invention is applied to the step of forming the extension regions of the transistor formed on the semiconductor substrate. However, the present invention is not limited to the formation of the extension regions. The manufacturing process of semiconductors contains various kinds of impurities injection steps such as a well injection step, a source/drain injection step, a pocket injection step, etc., and the present invention may be applied to these activating steps. Furthermore, accurate temperature control is required for the thermal treatment in the step of forming silicide, and the present invention may be applied to this thermal treatment. Still furthermore, the present invention may be applied to a process of heating a substrate having unevenness such as a thermal treatment process of FRAM capacitors, etc.

What is claimed is:

1. A thermal treatment method comprising:
    irradiating a surface of a treatment target with first light having diffusion property from plural directions by a first light source and determining light reflectance of the treatment target;
    adjusting the intensity of a second light of a second light source on the basis of the light reflectance, the second light has diffusion property; and
    irradiating the surface of the treatment target with the second light having adjusted intensity.

2. The thermal treatment method according to claim 1, wherein a light intensity distribution to a light irradiation angle of the first light of the first light source is equal to a light intensity distribution to a light irradiation angle of the second light of the second light source.

3. The thermal treatment method according to claim 1, wherein a wavelength band of the irradiation light of the first light source is equal to a wavelength band of the irradiation light of the second light source.

4. The thermal treatment method according to claim 1, wherein the treatment target is a semiconductor substrate, and a predetermined pattern is formed on the surface of the semiconductor substrate.

5. The thermal treatment method according to claim 2, wherein the light reflectance is determined by detecting a reflection light which is reflected from the surface of the treatment target from plural different directions upon incidence of first light of the first light source to the surface.

6. The thermal treatment method according to claim 5, wherein the light reflectance is determined by using an integral sphere.

7. The thermal treatment method according to claim 6, wherein the integral sphere includes:
    a convex portion reflecting the first light of the first light source; and
    a concave portion condensing a reflection light from the convex portion to the surface of the treatment target.

8. The thermal treatment method according to claim 6, wherein the integral sphere includes:
    an incident port being freely movable interlocking with the first light source and through which the first light of the first light is passed,
    wherein the light reflectance is determined by changing a light irradiation angle of the first light of the first light source by movement of the first light source, detecting the reflection light at each light irradiation angle of the first light of the first light source, weighting the reflectance of the reflection light at each light irradiation angle of the first light of the first light source by a light intensity distribution at a light irradiation angle of the second light of the second light source and averaging the weighted reflectance values to determine the light reflectance of the surface of the treatment target.

9. A method of manufacturing a semiconductor device comprising:
    doping impurities into a semiconductor substrate; and
    conducting a thermal treatment on the semiconductor substrate to activate the impurities;
    wherein the thermal treatment is executed on the semiconductor substrate by irradiating the semiconductor substrate with first light having diffusion property from plural directions by a first light source to determine a light reflectance of the semiconductor substrate, adjusting the intensity of a second light of a second light source having diffusion property on the basis of the light reflectance and irradiating the semiconductor substrate with the second light having adjusted the intensity of the second light.

10. The semiconductor device manufacturing method according to claim 9, wherein the light reflectance is determined by detecting a reflection light which is reflected from the surface of the treatment target from plural different directions upon incidence of first light of the first light source to the surface.

11. The semiconductor device manufacturing method according to claim 9, wherein the impurities are doped for an extension of an MOS transistor.

12. The semiconductor device manufacturing method according to claim 10, wherein the light reflectance is determined by using an integral sphere.

13. The semiconductor device manufacturing method according to claim 12, wherein the integral sphere includes:
    an incident port being freely movable interlockingly with the first light source, and the incident port through which the first light of the first light source is passed, and
    wherein the light reflectance is determined by changing a light irradiation angle of the first light of the first light source to the surface of the treatment target by movement of the first light source, detecting the reflection light at each light irradiation angle of the first light of the first light source, weighting the reflectance of the reflection light at each light irradiation angle of the first light of the first light source by a light intensity distribution at a light irradiation angle of the second light of the second light source and averaging the weighted reflectance values to determine the light reflectance of the surface of the treatment target.

* * * * *